United States Patent [19]
Kim

[11] Patent Number: 5,505,199

[45] Date of Patent: Apr. 9, 1996

[54] SUDDEN INFANT DEATH SYNDROME MONITOR

[76] Inventor: Bill H. Kim, 702 Doubletree La., Long Beach, Calif. 90815

[21] Appl. No.: 347,753

[22] Filed: Dec. 1, 1994

[51] Int. Cl.$^6$ .................................................. A61B 5/00
[52] U.S. Cl. ........................... 128/633; 128/716; 348/143
[58] Field of Search ..................................... 128/633, 664, 128/716, 721, 723; 348/143, 210–214

[56] References Cited

U.S. PATENT DOCUMENTS

| D. 284,697 | 7/1986 | Brefka | D24/17 |
|---|---|---|---|
| 4,146,885 | 3/1979 | Lawson, Jr. | 340/573 |
| 4,202,350 | 5/1980 | Walton | 128/690 |
| 4,409,983 | 10/1983 | Albert | 128/690 |
| 4,621,643 | 11/1986 | New, Jr. et al. | 128/663 |
| 4,653,498 | 3/1987 | New, Jr. et al. | 128/633 |
| 4,700,708 | 10/1987 | New, Jr. et al. | 128/633 |
| 4,765,340 | 8/1988 | Sakai et al. | 128/716 |
| 4,770,179 | 9/1988 | New, Jr. et al. | 128/633 |
| 4,802,486 | 2/1989 | Goodman et al. | 128/633 |
| 4,813,427 | 3/1989 | Schlaefke et al. | 128/671 |
| 4,851,816 | 7/1989 | Macias et al. | 340/573 |
| 4,862,144 | 8/1989 | Tao | 128/721 |
| 4,869,254 | 9/1989 | Stone et al. | 128/633 |
| 4,895,162 | 1/1990 | Dolliver | 128/721 |
| 4,911,167 | 3/1990 | Corenman et al. | 128/633 |
| 4,916,435 | 4/1990 | Fuller | 348/143 |
| 4,934,372 | 6/1990 | Corenman et al. | 128/633 |

(List continued on next page.)

FOREIGN PATENT DOCUMENTS

| 257955 | 4/1986 | France | 128/721 |
|---|---|---|---|

OTHER PUBLICATIONS

Weese–Mayer, MD et al, "Assessing Validity of Infant Monitor Alarms with Event Recording", *The Journal of Pediatrics*, Nov. 1989, vol. 115, No. 5, Part I, pp. 702–708.
Author Unknown, "Consensus Statement: National Institutes of Health Consensus Development Conference on Infantile Apnea and Home Monitoring, Sep. 29 to Oct. 1, 1986", *Pediatrics*, vol. 79, No. 2, Feb. 1987, pp. 292–299.
Hoffman, MA et al "Epidemiology of the Sudden Infant Death Syndrome: Maternal, Neonatal, and Postneonatal Risk Factors", *Clinics In Perinatology*, vol. 19, No. 4, Dec. 1992, pp. 717–737.
Spitzer, MD et al, "Home Monitoring", *Clinics In Perinatology*, vol. 19, No. 4, Dec. 1992, pp. 907–926.
Light, MB, MRCP et al, "Home Monitoring in Hawaii: The First 1,000 Patients", *Hawaii Medical Journal*, vol. 48, No. 8, Aug. 1989, pp. 304–310.
Poets, et al, "Home Monitoring of Transcutaneous Oxygen Tension in the Early Detection of Hypoxaemia in Infants and Young Children", *Archives of Disease in Childhood*, 1991; 66: pp. 676–682.
Author Unknown, "Position Statement: The Infant Home Monitoring Dilemma", *Can Med Assoc J*, Dec. 1, 1992; 147 (11), pp. 1661–1664.
Trond Markestad, "Information About Sudden Infant Death Syndrome for the General Public", *Acta Paediatrica Suppl*, 389: pp. 124–125, 1993.
Brochure from American SIDS Institute, Atlanta, Georgia.
David L. Bolam, MD, "Perinatal Page, Infant Home Apnea Monitoring: A Practical Review", *Nebraska Medical Journal*, Feb. 1992, pp. 34–37.

*Primary Examiner*—Angela D. Sykes
*Assistant Examiner*—Eric F. Winakur
*Attorney, Agent, or Firm*—Robbins, Berliner & Carson

[57] ABSTRACT

A sudden infant death syndrome, SIDS, monitor which monitors the infant to determine oxygen desaturation and movement. No alarm indication is produced if movement is detected, a low alarm condition is produced if desaturation occurs while movement is detected and a high condition is produced if desaturation is occurs and no movement is detected. A video monitor is provided to bring the image of the infant into the presence of the caregiver when either alarm is produced. The substantially reduced number of false alarms, due for example to motion artifacts, improves the level of alarm response over the long term that can reasonably be provided by parents and caregivers.

5 Claims, 5 Drawing Sheets

U.S. PATENT DOCUMENTS

| | | | |
|---|---|---|---|
| 4,955,379 | 9/1990 | Hall | 128/633 |
| 4,957,109 | 9/1990 | Groeger et al. | 128/640 |
| 5,022,402 | 6/1991 | Schieberl et al. | 128/671 |
| 5,025,791 | 6/1991 | Niwa | 128/670 |
| 5,099,702 | 3/1992 | French | 73/862 |
| 5,105,354 | 4/1992 | Nishimura | 364/413 |
| 5,107,845 | 4/1992 | Guern et al. | 128/664 |
| 5,134,284 | 7/1992 | Volgyesi | 250/252.1 |
| 5,143,078 | 9/1992 | Mather et al. | 128/716 |
| 5,151,945 | 9/1992 | Lee et al. | 382/1 |
| 5,206,807 | 4/1993 | Hatke et al. | 364/413 |
| 5,226,417 | 7/1993 | Swedlow et al. | 128/633 |
| 5,237,994 | 8/1993 | Goldberger | 128/633 |
| 5,241,300 | 8/1993 | Buschmann | 340/573 |
| 5,275,159 | 1/1994 | Griebel | 128/716 |
| 5,291,013 | 3/1994 | Nafarrate et al. | 250/227 |
| 5,295,490 | 3/1994 | Dodakian | 128/721 |
| 5,309,921 | 5/1994 | Kisner et al. | 128/719 |
| 5,368,026 | 11/1994 | Swedlow et al. | 128/633 |
| 5,389,967 | 2/1995 | Kim | 348/211 |
| 5,441,047 | 8/1995 | David et al. | 128/630 |

SUDDEN INFANT DEATH SYNDROME MONITOR

BACKGROUND OF THE INVENTION

1. Field of the Invention

This invention relates to monitors for Sudden Infant Death Syndrome (SIDS) and, in particular, relates to SIDS monitors configured to minimize false alarm problems from, for example, motion artifacts.

2. Description of the Prior Art

Sudden infant death syndrome is the medical terminology used to designate the almost inexplicable deaths of seemingly healthy infants. Commonly known as crib death, SIDS is the leading category of infant deaths between the ages of two weeks and one year and account for one-third of all deaths after the new born period.

Despite limited information, a scientific consensus suggests that SIDS occurred in healthy infants as a result of the simultaneous occurrence of a series of seemingly unrelated biological events. Infants who have periods of apnea, or difficulty in breathing, sudden skin color change to blue or pale, changes in muscle tone either to limpness or rigidity and who appear to require help in breathing are more likely to die of SIDS. These episodes can occur during sleep, feeding or while awake and are now known as apparent life-threatening events or ALTEs.

Specially designed apnea/bradycardia alarm systems became available for home use in the late 1970s to monitor infant breathing in an attempt to reduce SIDS. Conventional apnea/bradycardia monitors use electrodes attached to the infant's skin. The monitors provide an audible alarm if the baby stops breathing for a pre-determined period of time, or when the heart rate drops below a designated level, to indicate to the parent or guardian that the baby may need assistance in breathing. Conventional home monitors may now also include means for recording the electrocardiogram and respiratory wave form before, during or after the alarm event.

A number of scientific studies find a significant reduction in the incidence of SIDS in high risk groups utilizing home monitoring programs. However, conventional SIDS monitors are subject to many false alarms making it difficult for parents to maintain their watchfulness. The causes of such false alarms depends upon the type of monitor used. Transthoracic impedance based cardiorespiratory monitors, for example, are susceptible to cardiogenic artifacts. The resultant large number of false alarms, estimated to be on the order of 5 to 7 false alarms per monitoring period, substantially increases parental anxiety and therefore unfortunately reduces the likelihood that successful monitoring will be properly performed on a long term basis.

The pulse oximeter has been suggested for use as a SIDS monitor to monitor the blood hemoglobin oxygen saturation as a means of detecting hypoxemia secondary to apnea and hypoventilation as oxygen desaturation is the first event to occur in Sudden Infant Death Syndrome.

Conventional oxygen saturation monitors measure a light signal passed through an extremity that determines the wave length change created by oxygen containing red blood cells. Saturation probes are typically placed on the fingers, toes, hands or feet of the infant. Probe position on the infant's extremities therefore makes saturation measurements particularly susceptible to motion artifacts caused by movement of the infant. Positioning the probe electrodes on the infant's sternum or back has been proposed in an attempt to reduce the effects of infant movement.

In addition, various motion artifact compensating devices, such as accelerometers, have been developed for use with pulse oximeters used for other purposes. Unfortunately, motion artifacts still cause so many false alarms that the use of home oxygen saturation monitors is as frustrating to parents as other monitors even though oxygen saturation measurements hold out a substantial promise for reducing SIDS.

The integration of saturation monitoring with respiratory and cardiac monitoring has been also proposed. Nasal airflow, detected for example with a thermistor in the airflow path, are well known. Other types of respiratory measurements, not requiring the placement of a probe in the nasal passageway, have been developed to reduce the practical difficulties and inconvenience of the respiratory probe location.

Because of the high false alarm rate, the lack of clear understanding of the causes of SIDS and the resultant confusion about the most appropriate conditions to be monitored, physicians and parents have no clear path to pursue for protection. All that is really clear is that, when properly monitored, high risk infants have a better chance of survival.

What are needed are monitoring techniques that substantially increase the number of infants properly monitored and reduce the occurrence of false alarms in SIDS monitoring.

SUMMARY OF THE INVENTION

The present invention provides a SIDS monitor with substantially reduced false alarm difficulties in which a video monitor displays the infant in real time to the parents when oxygen desaturation is detected and produces a SIDS alarm if the infant is not then moving and a lower level of alarm if the infant is then moving.

In a first aspect, the present invention provides a SIDS monitor having an oxygen desaturation detector applied to an infant to be monitored, a movement detector for detecting movement of the infant, a video camera for monitoring the infant, a video display responsive to the video camera for displaying real time video images of the infant to a parent or other caregiver, and alarm processing circuitry for activating the video display when oxygen desaturation and movement are detected, and for activating the video display and producing a first level of alarm when oxygen desaturation is detected and movement is not detected.

In another aspect, the present invention provides a method of monitoring an infant for SIDS by detecting oxygen desaturation of an infant to be monitored, detecting movement of the infant, displaying real time video images of the infant to a parent or caregiver when oxygen desaturation is detected, and alerting the parent or caregiver with a first alarm when oxygen desaturation is detected if movement is not detected.

These and other features and advantages of this invention will become further apparent from the detailed description and accompanying figures that follow. In the figures and description, numerals indicate the various features of the invention, like numerals referring to like features throughout both the drawings and the description.

DETAILED DESCRIPTION OF THE PREFERRED EMBODIMENT(S)

Figure 1:
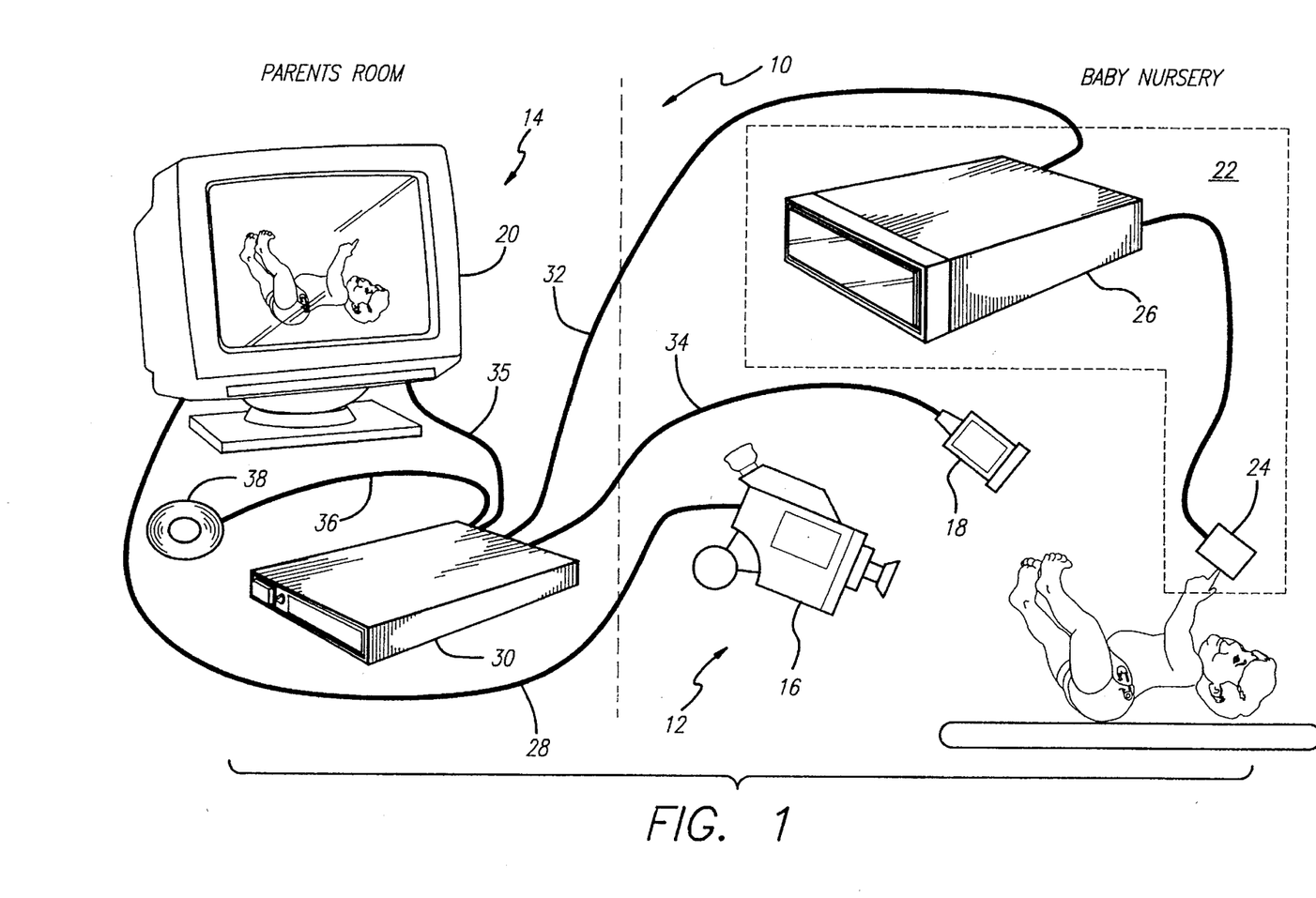
FIG. 1 is a pictorial schematic of a home SIDS monitoring system in accordance with the present invention.

FIG. 1 is a pictorial schematic of home SIDS monitoring system 10, in accordance with the present invention, including detection equipment 12 located in the nursery with the baby and alarm and display equipment 14 located in the parent's room or other convenient location for the caregiver. The overall operation of home SIDS monitoring system 10 may be understood from the timing graph described in greater detail with regard to FIG. 2.

Detection equipment 12 includes video camera 16 and non-contact motion sensor 18 focussed on the infant to be monitored. Video camera 16 may be any convenient type of video camera compatible with video display device 20 in alarm and display equipment 14 located in the parent's room to provide real video images of the infant being monitored. Non-contact motion sensor 18 may be a conventional infrared or ultrasonic sensor system and is described below in greater detail with respect to FIG. 3.

In addition to video camera 16 and non-contact motion sensor 18, detection equipment 12 in the nursery includes oxygen saturation detector 22 which is in contact with the infant. In particular, oxygen saturation detector 22 includes sensor probe 24 and saturation measurement system 26. Sensor probe 24 may contact the infant by being place on the infant's finger, toe, ear lobe or at some other convenient location. Oxygen saturation detector 22 is described in greater detail below with reference to FIG. 4.

Video signals from video camera 16 are provided by video cable 28 to video display device 20 in alarm and display equipment 14. Video display device 20 may be manually operated by means not shown but is otherwise under the control of alarm electronics 30 which is described in greater detail with regard to FIG. 5. Alarm electronics 30 receives as one input, an infant blood saturation level signal via oximeter data communication cable 32 from saturation measurement system 26. Alarm electronics 30 receives, as a second input, an infant motion indication signal via motion signal cable 34 from non-contact motion sensor 18. The video control output of alarm electronics 30 is connected via video alarm cable 35 to video display device 20. The audio alarm control output of alarm electronics 30 is connected via audio alarm cable 36 to audio alarm unit 38. A visual or other alarm may be added or substituted for the audio alarm. Audio alarm unit 38 is illustrated in the figures as a separate alarm unit, such as a loud speaker or siren, but for convenience may be located within video display device 20 or alarm electronics 30.

Figure 2:
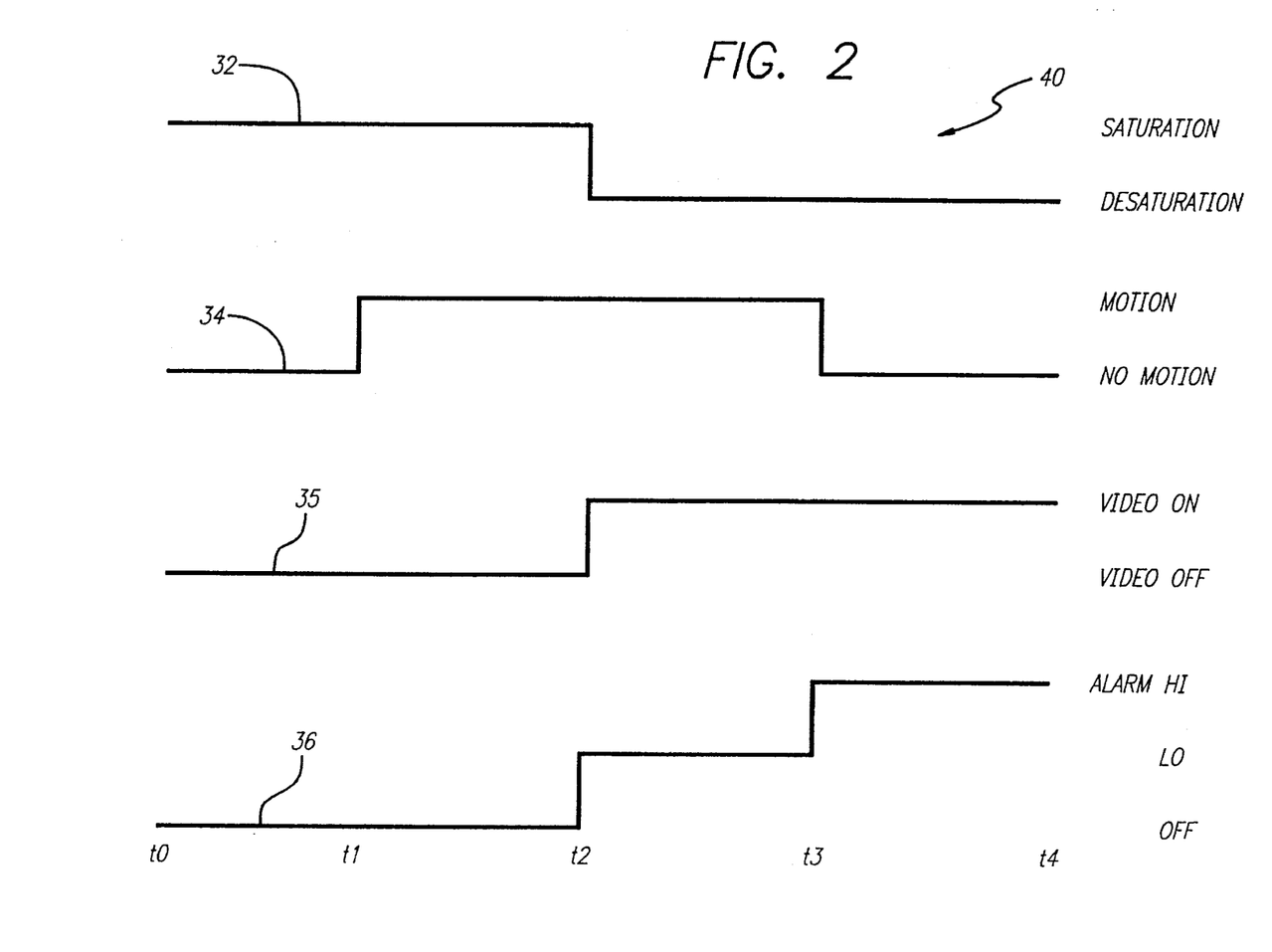
FIG. 2 is a timing graph illustrating the operation of home SIDS monitoring system 10 of FIG. 1.

Referring now to FIG. 2, the operation of alarm electronics 30— and therefore of home SIDS monitoring system 10— may best be understood from timing graph 40. The sequence of events depicted does not necessarily represent an ALTE, that is, a life threatening event, but rather illustrates the various possible conditions that may be detected by home SIDS monitoring system 10.

For example, from time t0 to time t2, the signal on oximeter data communication cable 32 is high indicating that oxygen saturation detector 22 has detected an oxygen saturation level, above an adjustable threshold, in the infant's blood. Alternatively, oxygen saturation detector 22 may provide data to alarm electronics 30 for comparison purposes. From time t2 through t4, however, the signal on oximeter data communication cable 32 indicates that the infant's blood is no longer properly saturated.

As long as the infant's blood is saturated, that is, from time t0 to time t2, the signal on video alarm cable 35 maintains video display device 20 in the off condition unless overridden by a manual control system not shown in this figure. Similarly, during this time period, audio alarm cable 36 maintains audio alarm unit 38 in an off condition.

When the infant's blood becomes desaturated with oxygen as detected by oxygen saturation detector 22, the signal on oximeter data communication cable 32 indicates desaturation. The condition of the video and audio alarms is then dependent upon whether or not motion is detected by non-contact motion sensor 18.

As a first example, the time period from time t2 to t3 is illustrated as one in which infant motion is detected and indicated on motion signal cable 34. During this time period, the signal on video alarm cable 35 causes video display device 20 to operate in an on condition while the signal on audio alarm cable 36 causes audio alarm unit 38 to produce a low level of audio alarm. As a result, the video is displayed to the parent who can gauge the magnitude of the infant motion.

The low level of audio alarm is intended to bring the parent or caregiver's attention to the video and to signify that although some attention should be paid to viewing the infant, an ALTE is not occurring. A typical cause of such a low level alarm would be desaturation caused by a motion artifact. That is, the normal motion of the infant has caused oxygen saturation detector 22 to indicate desaturation in error.

As a second example, however, the time period from time t3 to time t4 is illustrated as one in which infant motion is not detected. This is a much more serious event and may be considered to be an ALTE. As described above for the time period between time t2 and t3, the signal on video alarm cable 35 causes video display device 20 to operate in an on condition during the time period from time t3 to time t4. In addition, the signal on audio alarm cable 36 causes audio alarm unit 38 to produce a high level of audio alarm indicating danger. The high level of audio alarm is intended to bring the parent or caregiver's attention to the video display on video display device 20 long enough to verify that in fact the infant is not moving and/or sensor probe 24 has not fallen off the infant.

Thereafter it is expected that the parent or caregiver would immediately pick up the infant and attempt to determine what is wrong. Although the causes of SIDS have not been determined, it is well accepted that handling an infant during such an event is most likely beneficial and will cause the infant to begin to breathe again.

Figure 3:
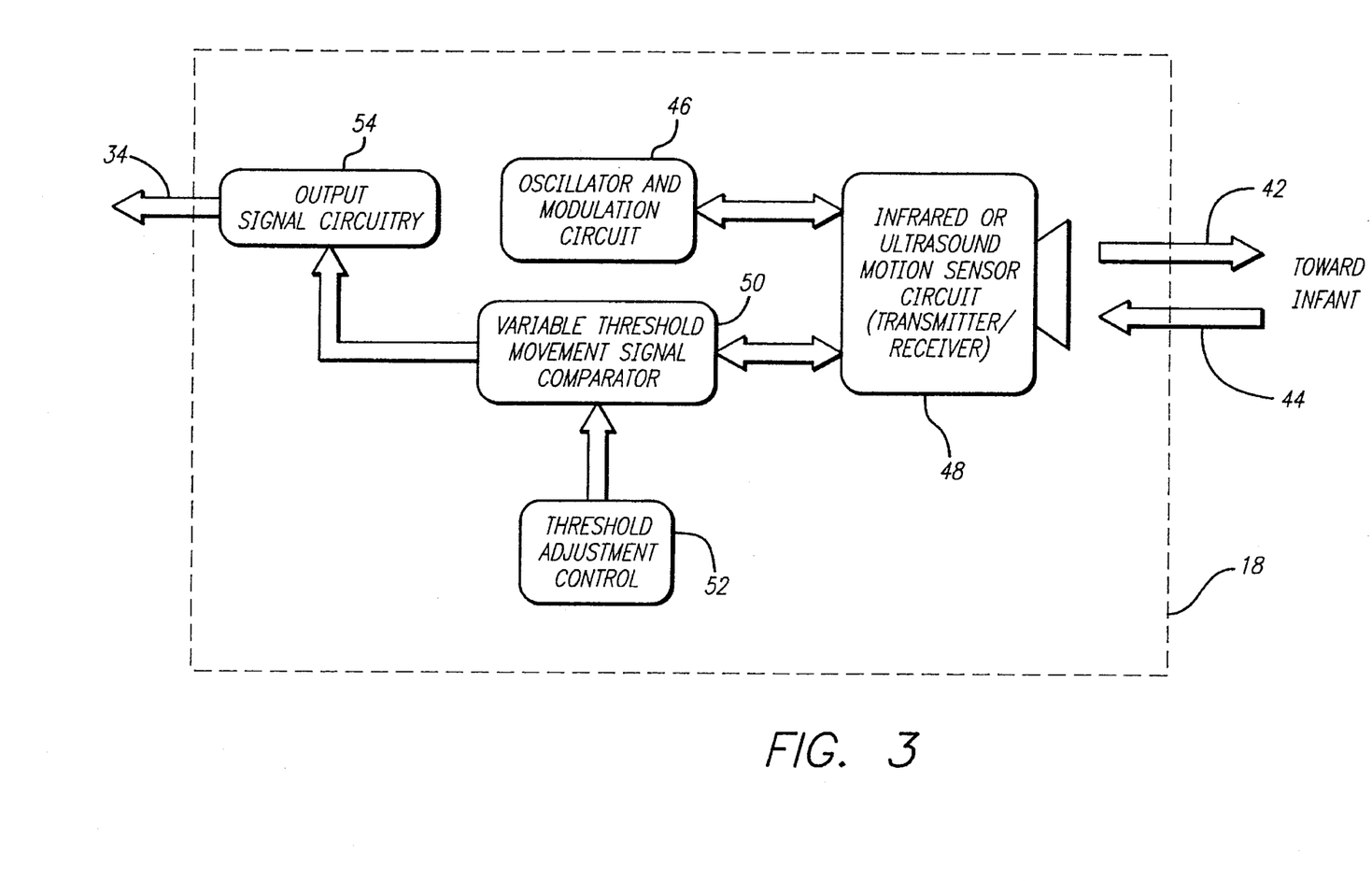
FIG. 3 is a flow diagram of the operation of non-contact motion sensor 18 shown in FIG. 1.

Referring now to FIG. 3, non-contact motion sensor 18 operates in a conventional manner by transmitting infra-red or ultra-sonic signals along transmit path 42 toward the infant and receiving the reflection of those signals along return path 44. The signals are produced in oscillator and modulator circuit 46 and transmitted and received via transducer 48. The reflected signal received along return path 44 is applied to comparator 50 together with a signal from threshold adjustment circuit 52. Adjustment of threshold adjustment circuit 52 allows the return signal to be compared against an adjustable threshold so that artifacts such as vibration and ambient thermal changes can be eliminated. The resultant output signal, indicating motion or no motion, is applied to motion signal cable 34 via output circuit 54.

Figure 4:
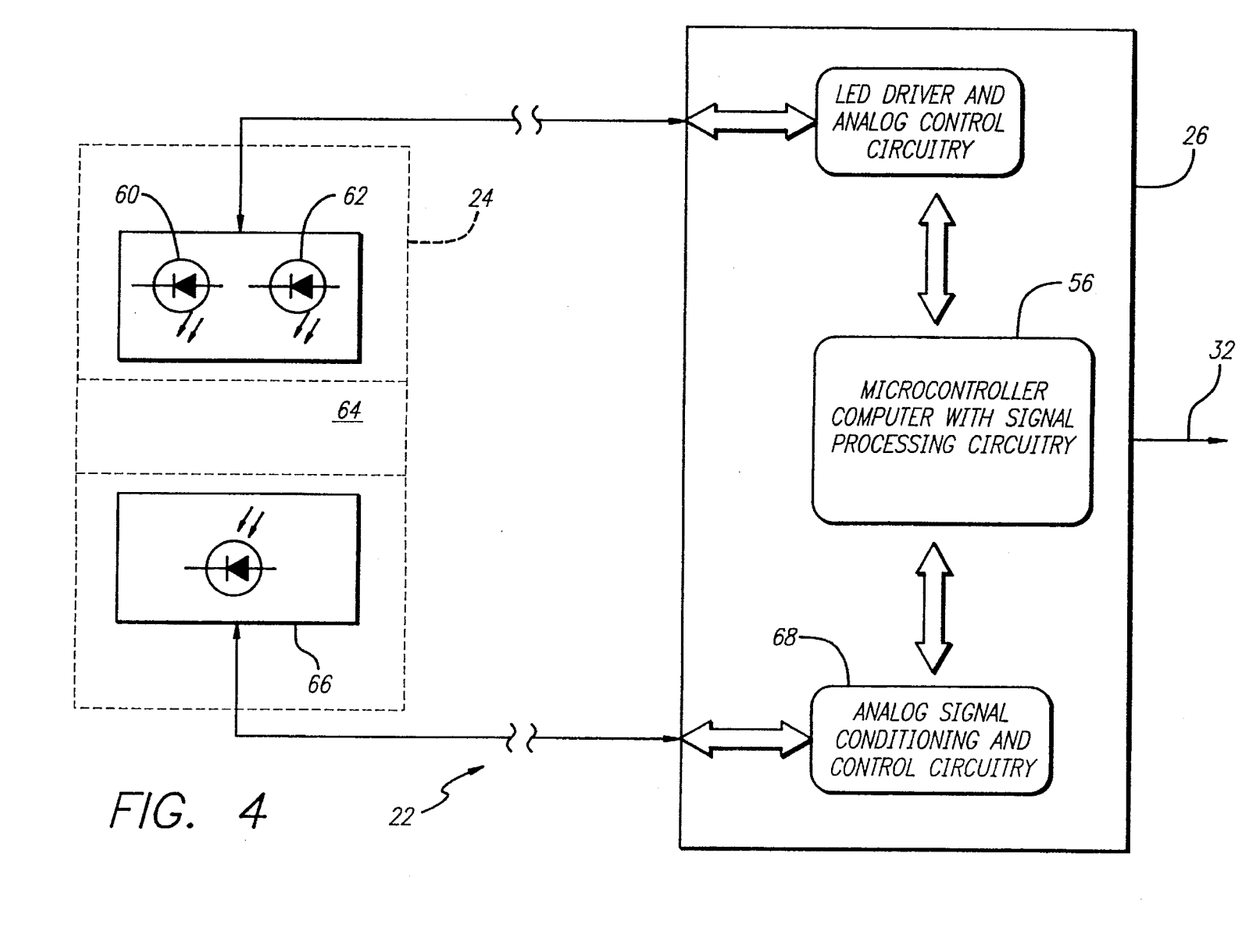
FIG. 4 is a block diagram of the operation of saturation measurement system 26 shown in FIG. 1.

Referring now to FIG. 4, oxygen saturation detector 22 is illustrated in greater detail including sensor probe 24 and saturation measurement system 26. Sensor probe 24 is depicted as a finger sensor for convenience although other conventional sensor probes may also be used. Saturation measurement system 26 operates under the control of microprocessor 56 which causes light emitting diode or LED driver 58 to illuminate LEDs 60 and 62 in sensor probe 24. LEDs 60 and 62 produce light at different frequencies or colors which react differently to the oxygen carrying portions of the blood.

After transmission through the finger of the infant, which is inserted within opening 64 of sensor probe 24, the light is collected by sensor 66 and applied via analog signal conditioning circuit 68 to microprocessor 56 in saturation measurement system 26. The state of saturation of the blood, that is, whether the blood is oxygen saturated or not, is determined by microprocessor 56 in accordance with known techniques and applied to oximeter data communication cable 32.

Figure 5:
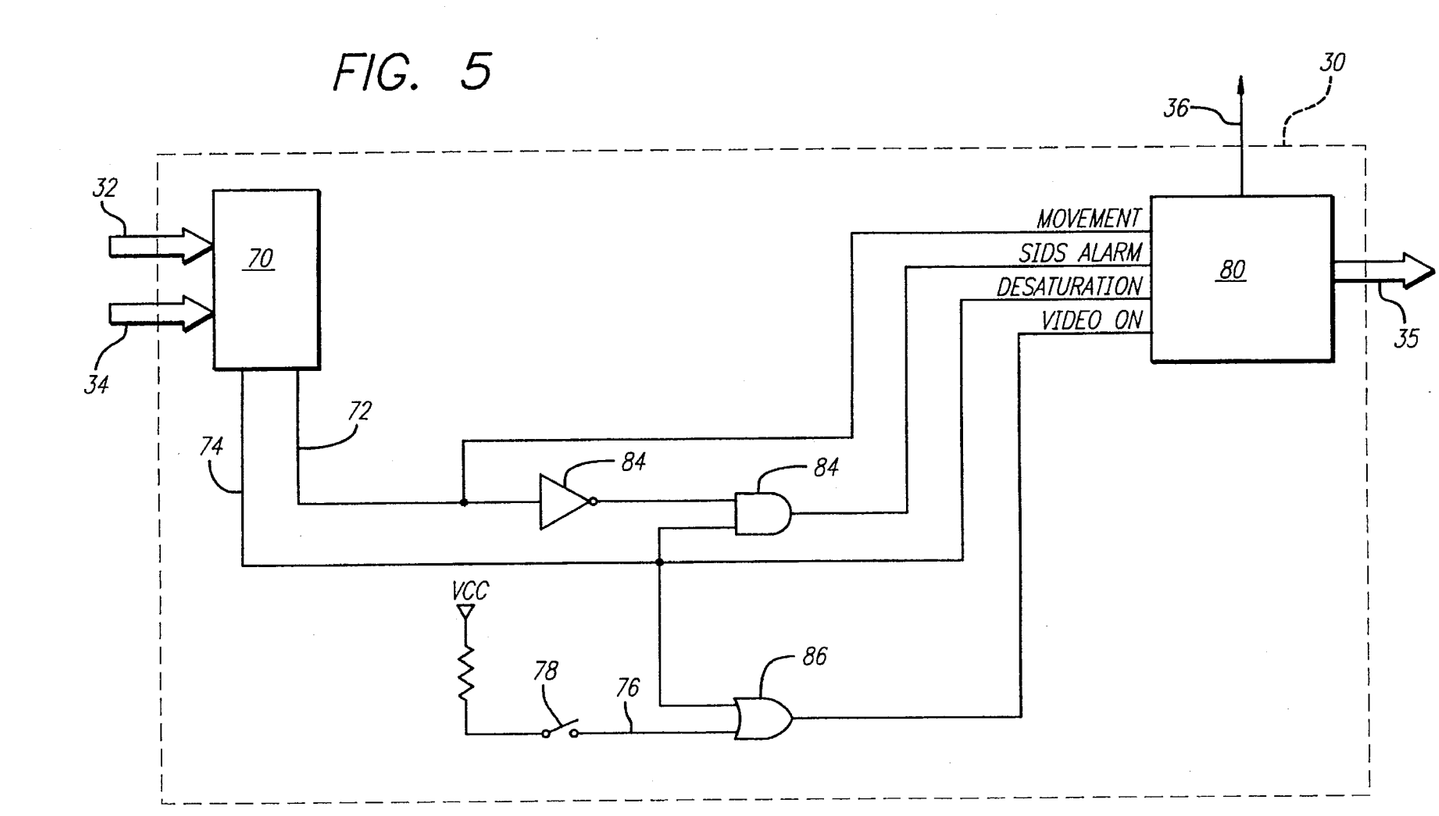
FIG. 5 is a logic diagram illustrating the operation of alarm electronics 30 shown in FIG. 1.

Referring now to FIG. 5, alarm electronics 30 is shown in greater detail including signal input conditioning circuit 70 which accepts as its inputs, the signals on oximeter data communication cable 32 and motion signal cable 34. Signal input conditioning circuit 70 produces movement detection signal 72 from the signal on motion signal cable 34 and desaturation detection signal 74 from the signal on oximeter data communication cable 32. The specific signal conditioning required in signal input conditioning circuit 70 depends on the exact nature of the signals applied to the input cables by saturation measurement system 26 and non-contact motion sensor 18.

Movement detection signal 72 and desaturation detection signal 74 are combined, together with manual video on signal 76 from manual override switch 78, to form the movement, SIDS alarm, desaturation alarm and video on inputs applied to alarm signal processing circuitry 80. In particular, movement detection signal 72 is applied directly to the movement input of alarm signal processing circuitry 80 and, after inversion by inverter 82, as one input to And gate 84.

Desaturation detection signal 74 is applied directly to the desaturation input of alarm signal processing circuitry 80, the second input of And gate 84 as well as on input of Or gate 86.

The second input for Or gate 86 is provided by manual video on signal 76 so that the output of Or gate 86 may be provided directly to the video on input of alarm signal processing circuitry 80. In this manner, when manual override switch 78 is activated to provide manual video on signal 76 or desaturation detection signal 74 indicates that the infant's blood is desaturated of oxygen below a predetermined level, a video on signal is provided to alarm signal processing circuitry 80 which commands video display device 20 to turn on via video alarm cable 35.

Similarly, the output of And gate 84 is applied to the SIDS alarm input of alarm signal processing circuitry 80 so that the SIDS audio alarm, that is the loud alarm, is sounded when both desaturation detection signal 74 indicates desaturation and movement detection signal 72 does not indicate movement. The SIDS audio or loud alarm, as well as the desaturation or soft alarm, are controlled by alarm signal processing circuitry 80 via audio alarm cable 36.

In operation, home SIDS monitoring system 10 therefore provides no alarm indications when oxygen saturation detector 22 indicates that the infant's blood is fully oxygenated. When oxygen saturation detector 22 detects desaturation, a soft alarm is sounded if infant motion is detected while a loud, SIDS alarm is sounded if infant motion is not detected. This operation permits the parent or caregiver to conveniently monitor the infant while substantially reducing the disruption produced by substantial false alarms. Rather than producing a false alarm apparently due to a motion artifact, or completely suppressing such false alarms while risking the suppression of a non-false alarm indicating a potential ALTE, the method and system of the present invention provide a compromise. The present invention provides a first alarm state when both desaturation and lack of motion indicate a potential ALTE and a second, lower level of alarm, when desaturation coupled with movement indicates either a potential problem or a motion artifact.

Having now described the invention in accordance with the requirements of the patent statutes, those skilled in this art will understand how to make changes and modifications in the present invention to meet their specific requirements or conditions. Such changes and modifications may be made without departing from the scope and spirit of the invention as set forth in the following claims.

What is claimed is:

1. A SIDS monitor comprising:

oxygen desaturation detector means adapted to be applied to an infant to be monitored for detecting oxygen desaturation of said infant;

movement detector means for detecting movement of the infant;

video camera means for producing real time video images of the infant;

video display means responsive to the video camera means for displaying said real time video images to a parent or other caregiver; and alarm processing circuitry means
for activating the video display means to display said real time video images when oxygen desaturation and movement are detected by said oxygen desaturation detection means and said movement detector mean, and
for activating the video display means to display said real time video images and for producing a first level of alarm, when oxygen desaturation is detected by said oxygen desaturation detection means and movement is not detected by said movement detector means.

2. The invention of claim 1, wherein the alarm processing circuitry means further comprises:

alarm circuitry means for activating a second level of alarm when oxygen desaturation and movement are detected by said oxygen desaturation detection means and said movement detector means, said second level of alarm being a lower level of alarm than said first level of alarm.

3. A method of monitoring an infant for SIDS, comprising the steps of:

detecting oxygen desaturation of an infant to be monitored;

detecting movement of the infant;

capturing real time images of the infant;

displaying said real time video images of the infant to a parent or caregiver when oxygen desaturation is detected; and alerting the parent or caregiver with a first alarm when oxygen desaturation is detected if movement is not detected.

4. The invention of claim 3, further comprising the step of:

alerting the parent or caregiver with a second alarm when oxygen desaturation is detected and movement is also detected.

5. The invention of claim 4, wherein the step of alerting the parent or caregiver with a second alarm further comprises the step of:

producing the second alarm at a lower level of alarm than the first alarm.

* * * * *